US008748162B2

(12) United States Patent
Hazlebeck et al.

(10) Patent No.: US 8,748,162 B2
(45) Date of Patent: Jun. 10, 2014

(54) SYSTEM AND METHOD FOR USING A PULSE FLOW CIRCULATION FOR ALGAE CULTIVATION

(71) Applicant: General Atomics, San Diego, CA (US)

(72) Inventors: David A. Hazlebeck, El Cajon, CA (US); Jiping Zhang, San Diego, CA (US); Xiaoxi Wu, Encinitas, CA (US)

(73) Assignee: General Atomics, San Diego, CA (US)

( * ) Notice: Subject to any disclaimer, the term of this patent is extended or adjusted under 35 U.S.C. 154(b) by 0 days.

(21) Appl. No.: 13/973,638

(22) Filed: Aug. 22, 2013

(65) Prior Publication Data

US 2014/0030796 A1 Jan. 30, 2014

Related U.S. Application Data

(62) Division of application No. 13/189,737, filed on Jul. 25, 2011, now Pat. No. 8,541,225.

(51) Int. Cl.
*C12N 1/12* (2006.01)
*C12N 1/00* (2006.01)

(52) U.S. Cl.
USPC .......................................... 435/257.1; 435/243

(58) Field of Classification Search
USPC .......................................... 435/257, 100, 243
See application file for complete search history.

*Primary Examiner* — Karen Cochrane Carlson
*Assistant Examiner* — Natalie Moss
(74) *Attorney, Agent, or Firm* — Nydegger & Associates

(57) ABSTRACT

A system and method for using a pulse flow to circulate algae in an algae cultivation apparatus are provided. In order to counteract the negative effects of biofouling on algae cultivation equipment, a pulse flow is created to periodically move through an algae cultivation apparatus. The pulse flow will dislodge algae cells adhering to various surfaces of the apparatus, and it will also create turbulence to stir up any algae cells which may have settled onto the bottom of the apparatus. To produce an increased fluid flow rate required to create an effective pulse flow, a sump, which is periodically filled with drawn algal culture from the apparatus, is located at an elevated position above the apparatus. When released, the algal culture travels through a transfer pipe and into the apparatus with gravity causing the algal culture to flow at a very high rate.

4 Claims, 2 Drawing Sheets

SYSTEM AND METHOD FOR USING A PULSE FLOW CIRCULATION FOR ALGAE CULTIVATION

This application is a divisional of application Ser. No. 13/189,737, filed Jul. 25, 2011, which is currently pending. The contents of application Ser. No. 13/189,737 are incorporated herein by reference.

FIELD OF THE INVENTION

The present invention pertains generally to systems and methods for growing algae. More particularly, the present invention pertains to the use of a system that can continuously grow algae in a more efficient manner by minimizing complications caused by biofouling. The present invention is particularly, but not exclusively, useful as a system for increasing the productivity of algae growth systems by using a pulse flow to periodically stir and rinse the algae cultivation apparatus.

BACKGROUND OF THE INVENTION

As worldwide petroleum deposits decrease, there is rising concern over petroleum shortages and the costs that are associated with the production of carbon-based fuel sources. As a result, alternatives to products that are currently processed from petroleum are being investigated. In this effort, biofuel has been identified as a possible alternative to petroleum-based fuels. In general, a biodiesel is a fuel comprised of mono-alkyl esters of long chain fatty acids derived from plant oils or animal fats. In industrial practice, biodiesel is created when plant oils or animal fats are reacted with an alcohol, such as methanol.

Apart from using animal fats, the creation of biofuels from plant oils has gained wide attention in recent years. The process of creating biofuel from plant oils, of course, necessarily begins by growing and harvesting plants such as algae cells. In particular, algae is known to be one of the most efficient plants for converting solar energy into cell growth, so it is of particular interest as a biofuel source.

In an algae cultivation system, the algae cells are typically grown in a cultivation apparatus as part of a liquid medium that is exposed to sunlight to promote photosynthetic growth. Further, the algae cell growth process normally requires the liquid medium to be continuously circulated through the system to allow algae cells to ingest nutrients. Three of the most prevalent algae cultivation apparatuses in use today which meet these requirements are: (1) a photobioreactor, (2) a cultivation pond with a circulation device, and (3) a cultivation pond without a circulation device. Despite having numerous advantages when growing algae, these apparatuses have significant disadvantages, many of which involve biofouling. With biofouling, algae cells tend to adhere to or accumulate on various surfaces. In particular, the algae cells adhere to a light transmitting cover and to the bottom and walls of the apparatus. Importantly, biofouling can significantly decrease the productivity of an algae cultivation system. In detail, if biofouling occurs because algae cells adhere to the light transmitting cover, photosynthesis is disrupted as less light reaches algae cells. In addition, when algae cells remain stationary on a surface, several problems arise: (1) algae cells may die and provide a food source for contaminants like protozoa; (2) algae cells settled too deep below the surface of the water will not receive enough light; and (3) algae cells will not move enough to ingest nutrients floating in the algal culture. All of these problems cause significant disruptions to an effective algae cultivation system.

Various efforts have been made to continuously circulate algal culture. Yet, biofouling still causes significant problems to algae cultivation systems. For one, system efficiency is hindered as algae cultivation systems must be drained and cleaned often to remove the algae cells that have adhered to various surfaces. These interruptions can be minimized by using a device or method that forcefully removes algae cells from surfaces and also serves as an impetus to circulate algae cells in the system.

In light of the above, it is an object of the present invention to provide a system and method for growing algae for biofuel production which minimizes the effects of biofouling. Another object of the present invention is to provide a system and method for growing algae that uses a pulse flow to increase the efficiency of the system. Yet another object of the present invention is to provide a system and method for growing algae using pulse flow circulation that is simple to implement, easy to use, and comparatively cost effective.

SUMMARY OF THE INVENTION

In accordance with the present invention, a system and method for using a pulse flow to circulate algae in an algae cultivation system is provided. An essential element of the present invention is the use of an elevated flush tank that is used to create the pulse flow. When it is created, the pulse flow circulates algae cells and dislodges any algae cells clinging to various components of the algae cultivation system.

Structurally, the system of the present invention may be adapted for use with any type of algae cultivation device presently in use, or the system may be used as a stand-alone algae cultivation system. The two most common devices for cultivating algae in use today are a photobioreactor or a pond (with or without a circulation device). The present invention can be adapted for use with either type of device. For comparison purposes, the photobioreactor is a closed system that most often has a vertical configuration, while the pond is an open system and is built in a horizontal configuration onto a surface. In either case, a flush tank is provided to store a fixed amount of algal culture effluent which has been drawn from the algae cultivation device. As contemplated for the present invention, the flush tank is situated higher than the cultivation device and is connected to the cultivation device by a conduit. To account for this difference in elevation, a circulation pump is provided to move the effluent from the cultivation device into the flush tank. This pump is usually located at an access point or a drainage point of the algae cultivation device. To be more specific, because a photobioreactor is usually constructed with a vertical orientation, an access or drainage point is most often situated at the bottom of the photobioreactor. And, a cultivation pond will have a designated drainage or access point for removing liquid from the pond. In either case, a conduit is connected between the circulation pump and the flush tank. In addition, a gas exchange tank may also be included in the system to add carbon dioxide ($CO_2$) to a portion of the drawn effluent while, at the same time, removing oxygen ($O_2$). The gas exchange tank is included in the system to promote algae growth by providing $CO_2$ to be used as a nutrient source by algae cells. As envisioned for the present invention, the gas exchange tank receives algal effluent drawn from the algae cultivation device, enriches the effluent with $CO_2$, and reintroduces the $CO_2$-rich effluent back into the cultivation device through a return pipe. Furthermore, the gas exchange tank and the flush tank can be the same one.

Several components may be provided to govern the release of the effluent from the flush tank. For one, a timer may be connected to the flush tank to release the effluent at a predetermined time. In another embodiment, a level switch is connected to the flush tank to release the effluent once the flush tank reaches a preplanned capacity level. As envisioned for the present invention, the timer and the level switch are both included for use with the system. Alternatively, the flush tank may also be manually activated with an activation switch. With any of the activation methods, a gate valve is moved from a closed position to an open position to release the fluid from the flush tank into a transfer pipe connected to the algae cultivation device. Upon activation, a pulse flows rapidly from the flush tank into the algae cultivation device.

In operation, the system of the present invention begins by drawing a portion of algal culture from the algae cultivation device to create an effluent. The effluent is then pumped, using the circulation pump, into the flush tank via the conduit. The effluent remains in the flush tank until it is released in one of the following ways: (1) the flush valve is manually opened; (2) the timer initiates the activator to open the flush valve; or (3) a level switch initiates the flush valve to release the effluent once the effluent reaches a predetermined level in the flush tank. It should be noted that the system may use any combination of the preceding methods for releasing effluent from the flush tank. Upon release, and due primarily to the elevation difference between the cultivation device and the flush tank, the effluent will flow rapidly out of the flush tank and into the cultivation device through a transfer pipe to create a pulse flow of effluent. Due to the sudden increase in the fluid flow rate, the pulse flow will dislodge any algae cells which are attached to any surface of the cultivation device. Additionally, the pulse flow will cause turbulence in the algae cultivation device. This turbulence will cause most, if not all, of the algae cells, which have settled onto the bottom of the cultivation device, to become suspended once again in the algal culture. This movement of the algae cells will promote photosynthesis and improve access to nutrients floating in the culture. In most cases, the direction of flow for the pulse flow will be the same direction as the flow in the cultivation device. Yet, the system may also reverse the flow direction of the pulse flow to go in the opposite direction of the algal culture flow in the cultivation device.

Once the effluent is released, the flush tank is emptied, and a new pulse flow cycle, or flush cycle, can begin. A new cycle begins when the flush valve is closed and the pump draws effluent to fill the flush tank.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
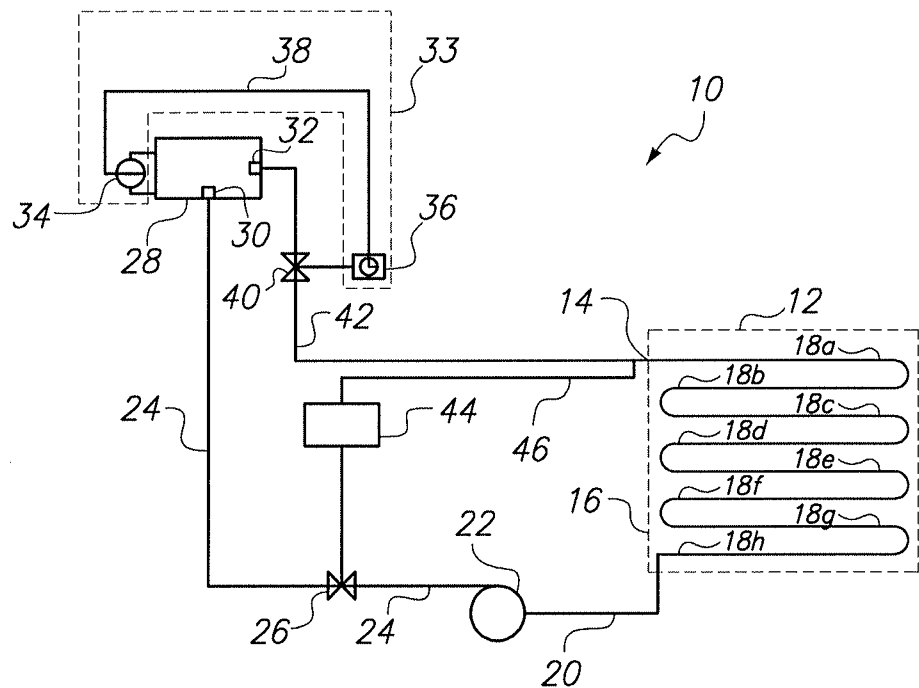
FIG. 1 is a schematic diagram of the layout of the system for the present invention when used in conjunction with a photobioreactor (PBR)

Initially referring to FIG. 1, a system of the present invention is shown and is generally designated 10. In FIG. 1, the system 10 is shown when used in conjunction with a photobioreactor 12 having an inlet 14 for introducing algal culture into the photobioreactor 12 and an outlet 16 for removing algal culture from the photobioreactor 12 as needed. In addition, the photobioreactor 12 is built with a plurality of flow channels 18*a-h* with algal culture traveling through the photobioreactor starting at flow channel 18*a*. As shown, the outlet 16 of the photobioreactor 12 is connected to a transfer pipe 20 through which circulation pump 22 can draw a portion of growing algal culture out of the photobioreactor 12. Furthermore, the circulation pump 22 is connected to a conduit 24 which includes a diverting valve 26 that is used to redirect algal culture from the conduit 24. The diverting valve 26 remains in a closed position when algal culture is being pumped to a flush tank 28, which is constructed with an inlet 30 and an outlet 32. As required for the present invention, the flush tank 28 stores drawn algal culture until released. In order to release the drawn algal culture, an activator 33 is provided. In FIG. 1, it can be seen that the activator 33 comprises a level switch 34 or a timer 36 electrically connected by a signal wire 38. Once initiated, the activator 33 will open gate valve 40 to release the drawn algal culture into a transfer pipe 42 connected between the flush tank 28 and the inlet 14 of the photobioreactor 12.

In order to promote algae growth, a gas exchange tank 44 is provided to provide $CO_2$ to algal culture in the photobioreactor 12. To do this, the diverting valve 26 is opened and effluent is pumped out of the photobioreactor 12. This effluent is diverted to the gas exchange tank 44 where $CO_2$ is added to the effluent and $O_2$ is removed. Once this gas exchange process is completed, the effluent from the gas exchange tank 44 will travel through a return pipe 46 to the photobioreactor 12 to provide nutrients to the growing algal culture. As envisioned for the present invention, diverting effluent to the gas exchange tank 44 can be accomplished independent of filling the flush tank 28 or at the same time as the flush tank 28 is filled, or the system can be arranged so that the flush tank is used for gas exchange purposes as well, and therefore the independent gas exchange tank 44 and the diverting valve 26 can be eliminated.

Figure 2:
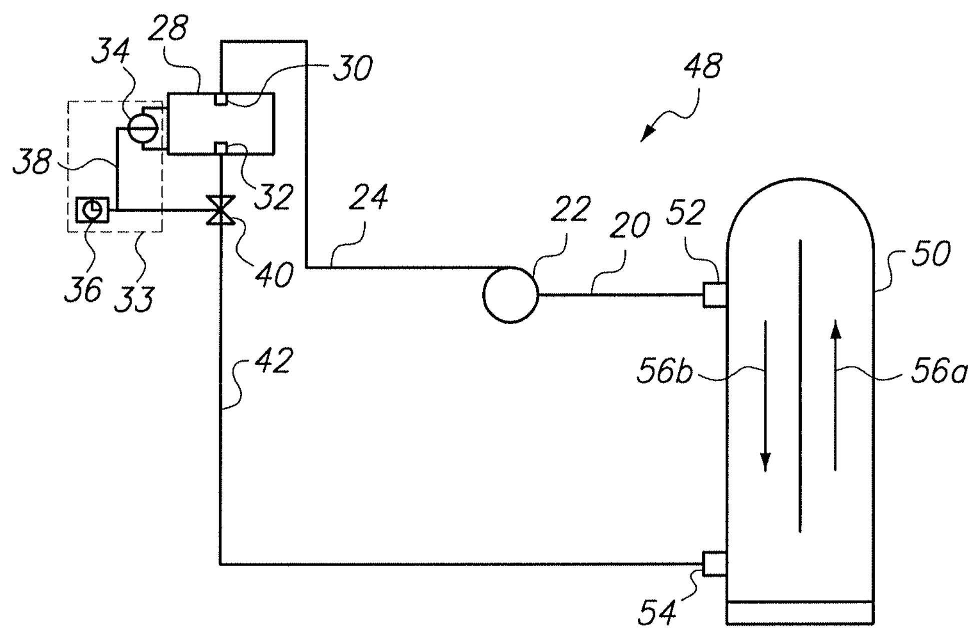
FIG. 2 is a schematic diagram of the layout of the system for the present invention when used in conjunction with a raceway pond with a circulation device.

Now referring to FIG. 2, a system 48 for the present invention, when used in conjunction with a raceway pond 50 containing algal culture, is shown. In this embodiment, many of the components are identical to the embodiment shown in FIG. 1. In the system 48, a circulation pump 22 removes an effluent of the algal culture out of the raceway pond 50 through a drainage point 52 into the transfer pipe 20. The effluent then moves through the circulation pump 22 and into the conduit 24 connected to the inlet 30 of the flush tank 28. Like the system 10 in FIG. 1, the activator 33, comprising a level switch 34 or a timer 36, controls the opening of the gate valve 40 which allows the effluent to be released from the flush tank 28 through its outlet 32. Once released, the effluent travels rapidly through transfer pipe 42 and into the raceway pond 50 through an inlet 54 to create a pulse flow. In system 48, the pulse flow will generate turbulence to force algae settled on the bottom of the raceway pond 50 off of the bottom and back into the culture which is flowing in the direction of arrows 56*a-b*. In addition, if the raceway pond 50 has a cover (not shown), algae attached to the cover will be dislodged and flow around the raceway pond 50.

Unlike the system 10 in FIG. 1, a gas exchange tank 44 is not required for the system 48 shown in FIG. 2 because the raceway pond 50 is an open system, unlike the photobioreactor 12 which is a closed system. Thus, carbon-based nutrients are easier to add directly to an open system like the raceway pond 50. But, a gas exchange tank 44 and associated equipment (i.e. diverting valve 26 and return pipe 46) can be added to the system 48, if desired, in a similar configuration as shown in FIG. 1. Alternatively, the gas exchange can take place in the flush tank 28.

Figure 3:
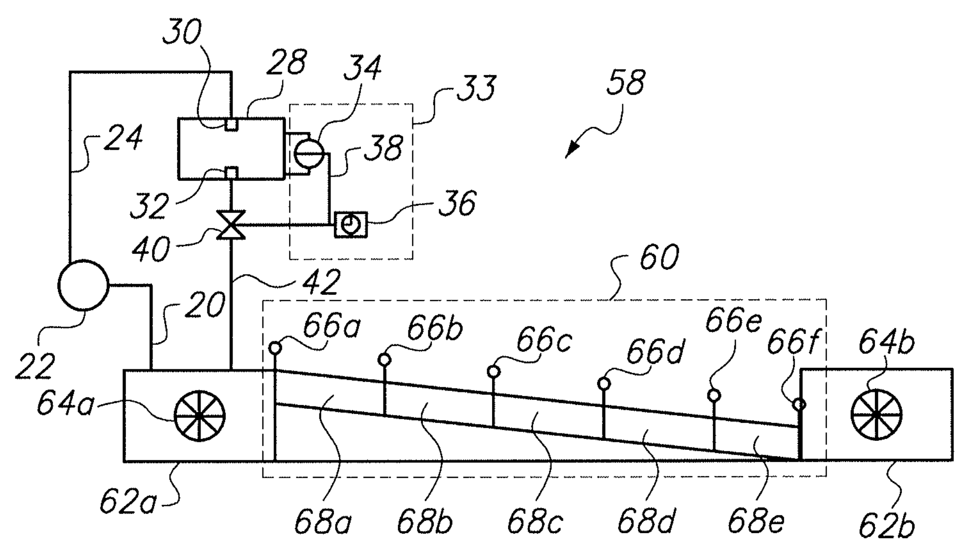
FIG. 3 is an elevation view of the system of the present invention when used in conjunction with a sloped pond without a circulation device.

Now referring to FIG. 3, a system 58 is shown when adapted for use with a sloped pond 60. As can be seen, the circulation pump 22, the flush tank 28, level switch 34, timer 36, and gate valve 40 are substantially identical and operate in the same manner as systems 10 and 48 in FIG. 1 and FIG. 2 respectively. Importantly, the pulse flow is created in the same manner with effluent being released from the flush tank 28. Instead of entering a photobioreactor 12 or a raceway pond 50, the pulse flow enters a sump 62*a* before reaching the sloped pond 60. When a sloped pond 60 is used for algae cultivation, a main pump 64*a*, housed within the sump 62*a*, is provided to initiate fluid flow. As shown in FIG. 3, the sloped pond 60 is constructed with a plurality of flush gates 66*a-f*, with the area between consecutive flush gates 66*a-f* being referred to as a segment 68*a-e*. At the end of the last segment 68*e*, sump 62*b*, housing another main pump 64*b*, leads to another sloped pond (not shown). It should be noted that the system 58 may also be constructed with flush gate 66*a* only. With only flush gate 66*a*, the pulse flow will travel through the entire length of the sloped pond 60 when released from the flush tank 28. When using a plurality of flush gates 66*a-f*, the pulse flow can be controlled as all of the flush gates 66*a-f* can be opened simultaneously (in the same manner as when only flush gate 66*a* is used), or the flush gates 66*a-f* can be opened one at a time. If one flush gate is opened at a time, the pulse flow will travel through one segment 68*a-e* at a time.

Still referring to FIG. 3, an alternate embodiment may also be described. In this alternate embodiment, the flush tank 28 is replaced by the sump 62 and houses pump 64*a*. In this configuration, the circulation pump 22 can be eliminated because pump 64*a* is configured to produce the pulse flow. With the height of the flush tank 28 eliminated, pump 64*a* will be constructed to compensate for the lack of gravity flow by having the ability to produce the high fluid flow rate required to produce the pulse flow. Without a flush tank 28, the level switch 34 or timer 36 are incorporated with the sump 62 and main pump 64*a*. In this arrangement, the main pump 64*a* is configured to create a pulse flow, and instead of a gate valve 40, the flush gate 66*a* serves to release the effluent from the sump 62. The level switch 34 or timer 36 can be set to open the flush gates 66*a-f* in any sequence.

Figure 4:
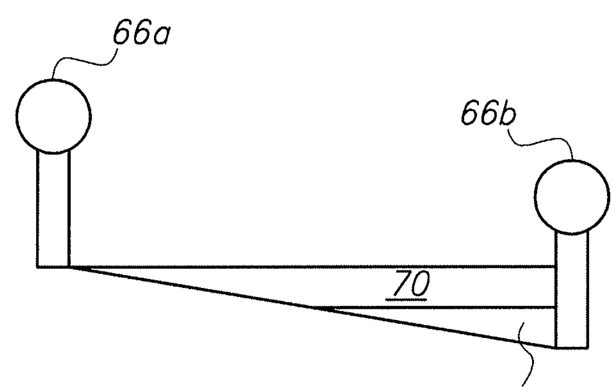
FIG. 4 is a detail of one section of the system of the present invention when used in conjunction with a sloped pond.

Referring now to FIG. 4, a detail of a segment between two flush gates 66*a-b* is shown. In FIG. 4, the concept of light and dark cycles is illustrated. In more detail, when flush gates 66*a-b* are in a closed position, a portion of effluent remains between the flush gates 66*a-b*. As shown, the effluent between the gates 66*a-b* will generally settle in two layers or zones, a light zone 70 and a dark zone 72. Algae cells in the effluent which settle in the light zone 70 will have an increased exposure to the light necessary for photosynthesis. At the same time, the algae cells which settle in the effluent in the dark zone 72 are not exposed to enough light for photosynthesis to occur. By using the pulse flow to create turbulence to stir up, or mix, the algal culture, nearly all of the algae cells will be exposed to a suitable amount of light for photosynthesis during one or more flush cycles.

While the System and Method for Using a Pulse Flow Circulation for Algae Cultivation as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for using a pulse flow to circulate algae in an algae cultivation apparatus which comprises the steps of:
- cultivating an algal culture in an algae cultivation apparatus;
- circulating the algal culture using the algae cultivation apparatus;
- transferring a portion of algal culture to a flush tank using a circulation pump, wherein the portion of algal culture being transferred is an effluent;
- flushing the effluent from the flush tank into the algae cultivation apparatus by initiating an activator to allow for gravity flow of the effluent from the flush tank into the algae cultivation apparatus via a transfer pipe having a first end and a second end, wherein the first end of the transfer pipe connects to the flush tank and the second end of the transfer pipe is positioned in the algae cultivation apparatus;
- wherein the activator is a device selected from a group comprising a timer and a level switch,
- wherein said device is connected to the flush tank, to open a gate valve to allow the effluent to enter the transfer pipe.

2. The method as recited in claim 1 wherein the cultivating step is accomplished using a sloped pond, wherein the sloped pond is constructed with a plurality of flush gates.

3. The method as recited in claim 2 further comprising the step of activating the flush gates in sequence.

4. The method as recited in claim 2 further comprising the step of activating the plurality of flush gates simultaneously.

* * * * *